United States Patent [19]

Schryver

[11] Patent Number: 5,226,917
[45] Date of Patent: Jul. 13, 1993

[54] ACETABULAR PROSTHESIS WITH ANCHORING PEGS

[75] Inventor: Jeff Schryver, Cordova, Tenn.

[73] Assignee: Smith & Nephew Richards Inc., Memphis, Tenn.

[21] Appl. No.: 656,247

[22] Filed: Feb. 14, 1991

[51] Int. Cl.⁵ .............................................. A61F 2/34
[52] U.S. Cl. ........................................ 623/22; 623/18
[58] Field of Search ................ 623/16, 18, 20, 22, 623/23; 606/69, 70

[56] References Cited

U.S. PATENT DOCUMENTS

| | | | |
|---|---|---|---|
| 3,939,497 | 2/1976 | Heimke et al. | 3/1.912 |
| 4,013,071 | 3/1977 | Rosenberg | 623/16 |
| 4,484,570 | 11/1984 | Switter et al. | |
| 4,563,778 | 1/1986 | Roche et al. | 623/22 |
| 4,566,138 | 1/1986 | Lewis et al. | 623/22 |
| 4,685,923 | 8/1987 | Mathys | 623/22 |
| 4,792,337 | 12/1988 | Muller | 623/22 |
| 4,828,565 | 5/1989 | Duthoit et al. | 623/22 |
| 4,923,473 | 5/1990 | Griss et al. | 623/22 |
| 4,955,325 | 9/1990 | Zarnowski et al. | 623/22 |
| 4,955,917 | 9/1990 | Karpf | 623/22 |
| 4,990,161 | 2/1991 | Kampner | 623/22 |

FOREIGN PATENT DOCUMENTS

| | | |
|---|---|---|
| 0013863 | 1/1979 | European Pat. Off. . |
| 0169978 | 4/1985 | European Pat. Off. . |
| 0211169 | 5/1986 | European Pat. Off. . |
| 0212087 | 5/1986 | European Pat. Off. . |
| 0341198 | 3/1989 | European Pat. Off. . |
| 0393543 | 10/1990 | European Pat. Off. ............. 623/22 |
| 2318459 | 10/1974 | Fed. Rep. of Germany ........ 623/22 |
| 2638963 | 5/1990 | France .................................. 623/22 |
| 1170295 | 11/1969 | United Kingdom . |
| 2080118 | 2/1982 | United Kingdom . |

*Primary Examiner*—David Isabella
*Attorney, Agent, or Firm*—Pravel, Hewitt, Kimball & Krieger

[57] ABSTRACT

An improved acetabular cup prosthesis has a cup body with a plurality of bores extending between an inner concave surface and an outer convex surface, wherein the bores can function as drill guides for providing alignment in the drilling of surgical openings after the acetabular cup body is placed in a patient. A plurality of pegs or spikes have proximate end portions that have connection members for forming connections with the bores, and distal end portions that can register into the drilled surgical openings.

18 Claims, 7 Drawing Sheets

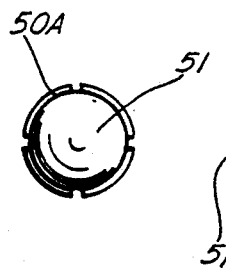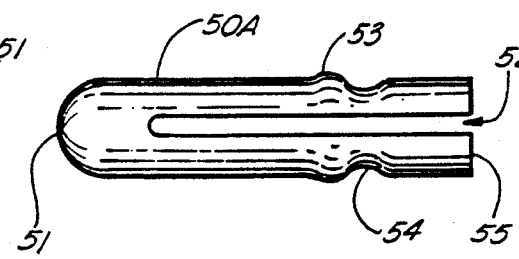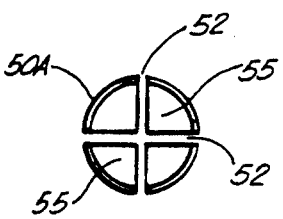
FIG. 5A    FIG. 5B    FIG. 5C
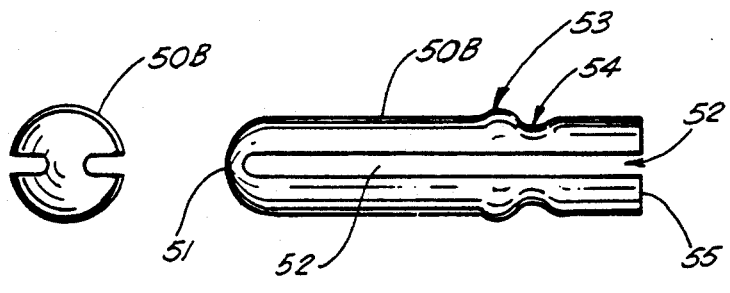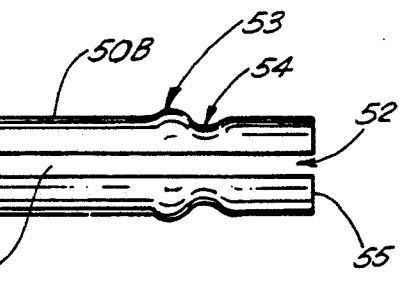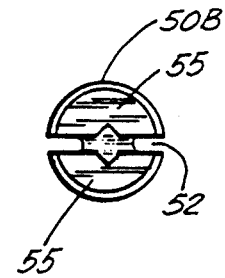
FIG. 6A    FIG. 6B    FIG. 6C
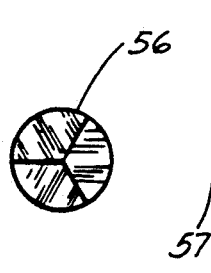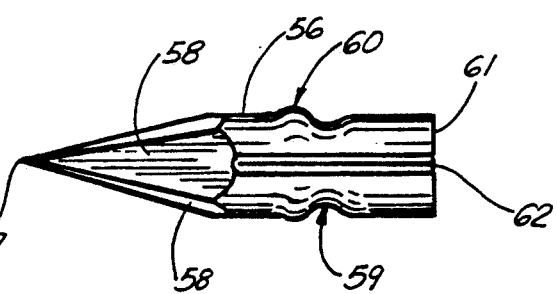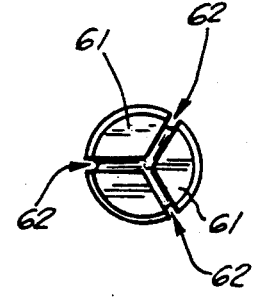
FIG. 7A    FIG. 7B    FIG. 7C

ACETABULAR PROSTHESIS WITH ANCHORING PEGS

BACKGROUND OF THE INVENTION

1. Field Of The Invention

The present invention relates to acetabular prosthetic devices and more particularly to an improved acetabular prosthesis that includes radially extending bores therethrough that can be used as drill guides by a surgeon after the acetabular cup has been placed in the patient, and wherein holes can be drilled surgically into the underlying bone tissue so that one or more pegs for improved anchoring can be placed into the bores and anchored into the underlying surgical openings.

2. General Background

There are a number of commercially available acetabular prosthetic devices that include a cup shaped body, some of which have projections extending from the outer surface of the cup-shaped body. For example, U.S. Pat. No. 3,939,497 describes a socket for a hip joint prosthesis which is secured to a cavity in the bone tissue by a series of radially arranged pegs which can be projected outwardly from the wall of the socket into the surrounding tissue by a central screw which also has a self-tapping thread that enters the tissue.

U.S. Pat. No. 4,685,923 provides a hip joint socket made from a plastics material that can be installed without the use of bone cement or adhesive. The socket comprises a hemisphere of polyethylene. The socket may have four bores extending skewed to the equatorial plane to permit the surgeon to fix the socket in the acetabulum by means of screws or dowels temporarily or permanently. The primary anchoring is provided by two plugs or pins arranged on the outer surface of a socket. The pins may be substantially parallel to each other. The pins are inserted in bore holes drilled into the bone. The bore holes are drilled so that the pins are inserted under stress. A secondary anchor in the form of flaps are present near the actuarial plane of the socket. These flaps supplement the anchoring affect of the pins.

In U.S. Pat. No. 792,337 an acetabular cup is provided which has a metallic anchoring shell. The cup is for cement-less fixation in the acetabulum. The shell has several holes through which screws are driven into the bone. The screws have rounded heads and the holes are countersunk so that the orientation of the screws may be varied with respect to the cup and each other.

In U.S. Pat. No. 4,828,565 there is provided a cotyliodal component for a non-cemented hip prosthesis. The component has two parts, a titanium hemispherical shell and a cup of polymer which is engaged into it. The shell has two zones, the first zone is covered with porous titanium capable of being invaded by spongy bone and also has two projecting pieces. The other zone has a smooth metal surface. Two screws pass through the projecting pieces and are used to anchor the component in the acetabulum.

Another acetabular cup for cement-less fixation in the acetabulum is described in European Patent Application No. 13,863, published Jun. 8, 1980. The cup is anchored to the bone by a central pin and a number of other pins distributed over the surface of the cup. The pins have several sawtooth notches along their length. The bone may be pre-drilled to take the pins.

European Patent Application No. 169,978 published May 2, 1986, describes an acetabular cup which has an outer shell embedded into the patient's pelvis. The outer shell has a frustro-conical skirt and a spherical central cap. The shell has a number of small tufts with rounded ends projecting from its surface. The tufts are embedded in the bone tissue to provide improved anchorage.

In European Patent Application No. 211,169 published Feb. 25, 1987, an acetabular cup is described in which an external boss protrudes from the outer surface of the acetabulum body to fit into a pre-drilled hole in the acetabulum. The cup also has two anchoring lugs in the meridian plane. The lugs take screws to aid in anchoring the cup.

Other foreign patents and patent applications which describe acetabular cups include European Patent Application No. 212,087 published Apr. 3, 1987, wherein metallic pins project from the surface of the cup and contain holes in which tissue may grow. In European Patent No. 341,198 published Nov. 8, 1989, an acetabular cup has a metal outer shell and a plastics body for retaining the hip joint head. The shell is frustro-conical in cross-section with an opening at an apex and circular teeth around the outside. Three or more anchoring dowels parallel to the convexes protrude from the outer surface of the shells. The dowels are slotted and provide with circular teeth of a sawtooth cross-section over the portions which protrude. A central bolt may be fitted into the dowel to provide a rounded end.

The use of cement for fixation of acetabular process, and in some cases the use of spacers, is found in U.S. Pat. Nos. 4,563,778, and 4,566,138. This concept of the use of bone cement and spacers is also seen in United Kingdom Patent Nos. 1,170,295 and 2,080,118.

U.S. Pat. No. 4,923,473, issued to Peter Griss et al., entitled "Hemispherical Acetabulum", relates to a hemispherical acetabulum having a fixing pin which projects from the outside surface of the acetabulum.

In prior art acetabular cup prosthetic devices, the projections or spacers are often for the sole purpose of providing a space from the bone tissue that can be occupied by bone cement. Further, many acetabular cup prosthetic devices carry projections on their outer surface which are a part of the prosthesis as constructed and which cannot be added thereafter.

Still other prosthetic devices in the form of acetabular cups provide pegs which must be affixed to the tissue before the acetabular cup is placed in the position.

SUMMARY OF THE PRESENT INVENTION

The present invention provides an improved acetabular cup prosthesis wherein the prosthesis body or shell with pegs having attachment to the shell. The shell preferably includes openings therethrough which can function as drill guides for the surgeon after the cup has been placed in a patient. The present invention affords improved fixation and stability of the component because pegs or spikes can be placed in the acetabular cup body after it has been placed in position by the surgeon. The pegs or spikes can be easily removed and easily installed from the concave side of the acetabular cup body component notwithstanding the fact that the acetabular cup body component has already been placed in operative position in the patient.

With the present invention, a multiplicity of pegs or spikes can be rigidly attached to an acetabular cup prosthesis body for the purpose of securing it in place in the acetabular bone. This can be done through an opening or bore which is interchangeably used for a desired peg or spike. A bone screw can be used through one of the openings if desired.

With the present invention, the acetabular cup can be placed in its desired position in the pelvis by the surgeon. The pegs as described more fully herein are then added to the cup body and attached to the prosthesis in a rigid fashion. The peg or spike protrudes through the acetabular cup body and into the underlying bone tissue of the acetabulum to provide a mechanical locking of the acetabular cup component into the pelvis. The surgeon can use a pre-drill before placing the peg or spike wherein the opening or bore in the acetabular cup body functions as a drill guide. Pegs can be selectively placed so that they are not aligned with each other but are at angles to each other which aids in the mechanical stability of the acetabular cup body.

The apparatus uses a plurality of pegs or spikes that can be of different shapes and which can use a taper lock, barb lock, knurl lock, or screw lock or compression friction lock for forming a connection with the bores or openings in the acetabular cup body.

The present invention thus provides an improved acetabular cup prosthesis that includes an acetabular cup body or shell component, having an inner concave surface and an outer convex surface. A plurality of openings extend between the inner and outer surfaces along radial lines that can merge at or near the center of curvature of the inner concave surface of the cup body, the openings forming elongated bores surrounded by a bore wall portion of the acetabular cup body. The cup body or shell can be spherical in form, or not spherical in form (such as e.g., an egg-shaped cup or shell).

The openings are positioned to define one or more drill guides so that the surgeon can selectively drill into the underlying tissue through one or more of the openings and form surgical openings therein in the underlying bone tissue.

There are preferably a plurality of peg members, each being insertable into and registering with one or more of the openings in the prosthesis body, the peg members having a first proximate end portion having means thereon for forming a connection with the acetabular cup body at one of the openings and with the bore wall, and a second distal end portion adapted to extend into the underlying tissue (e.g., into surgically formed openings) after the cup body has been implanted in a patient.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIGS. 5A-5C are bottom, side, and top views of peg portion of the preferred embodiment of the apparatus of the present invention;

FIGS. 6A-6C are bottom, side, and top views of another peg as used with the preferred embodiment of the apparatus of the present invention;

FIGS. 7A-7C are bottom, side, and top views of a spike member as used with the preferred embodiment of the apparatus of the present invention;

DETAILED DESCRIPTION OF THE PREFERRED EMBODIMENT

Figure 1:
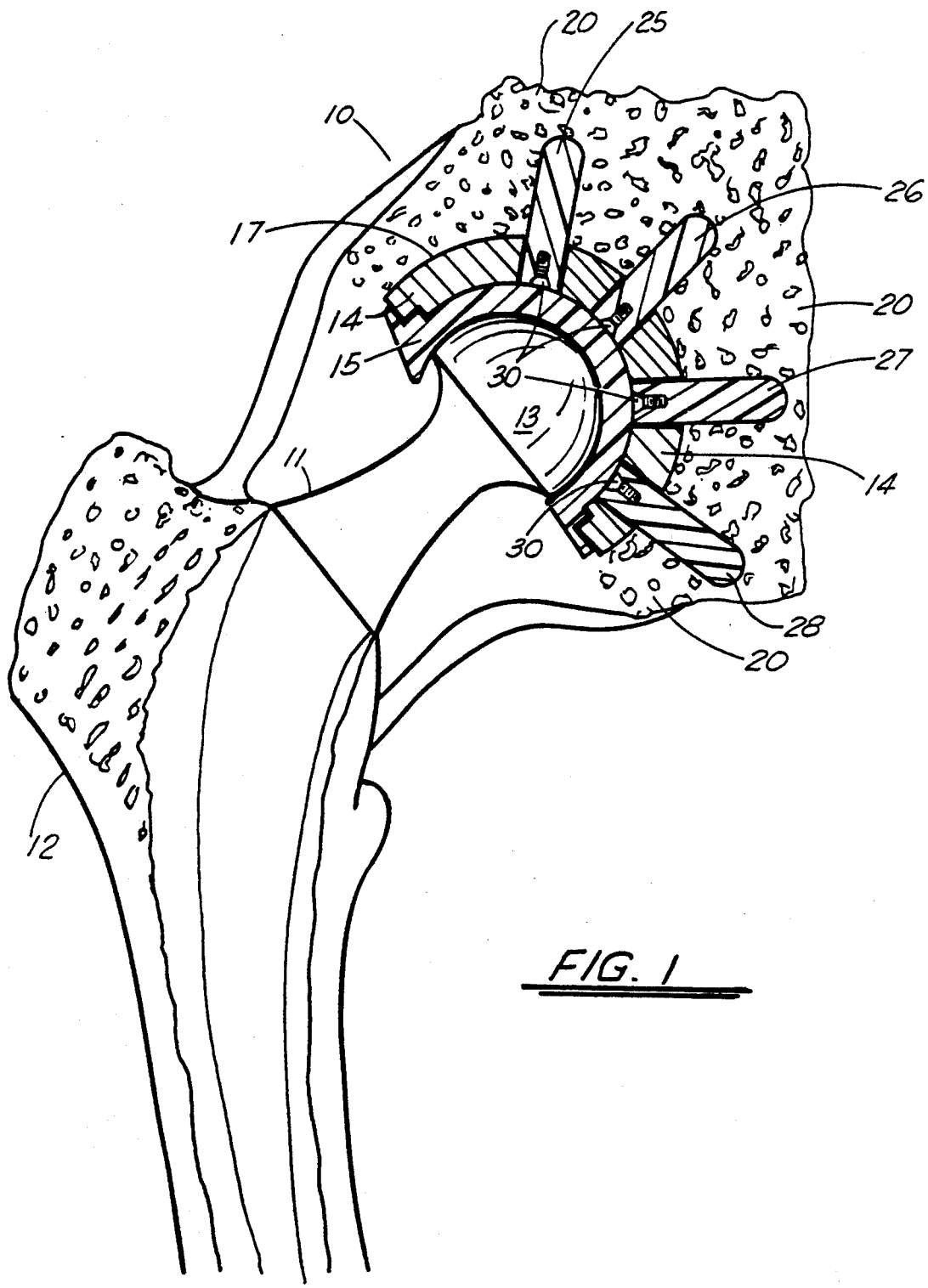
FIG. 1 is a side sectional view of the preferred embodiment of the apparatus of the present invention.
Figure 2:
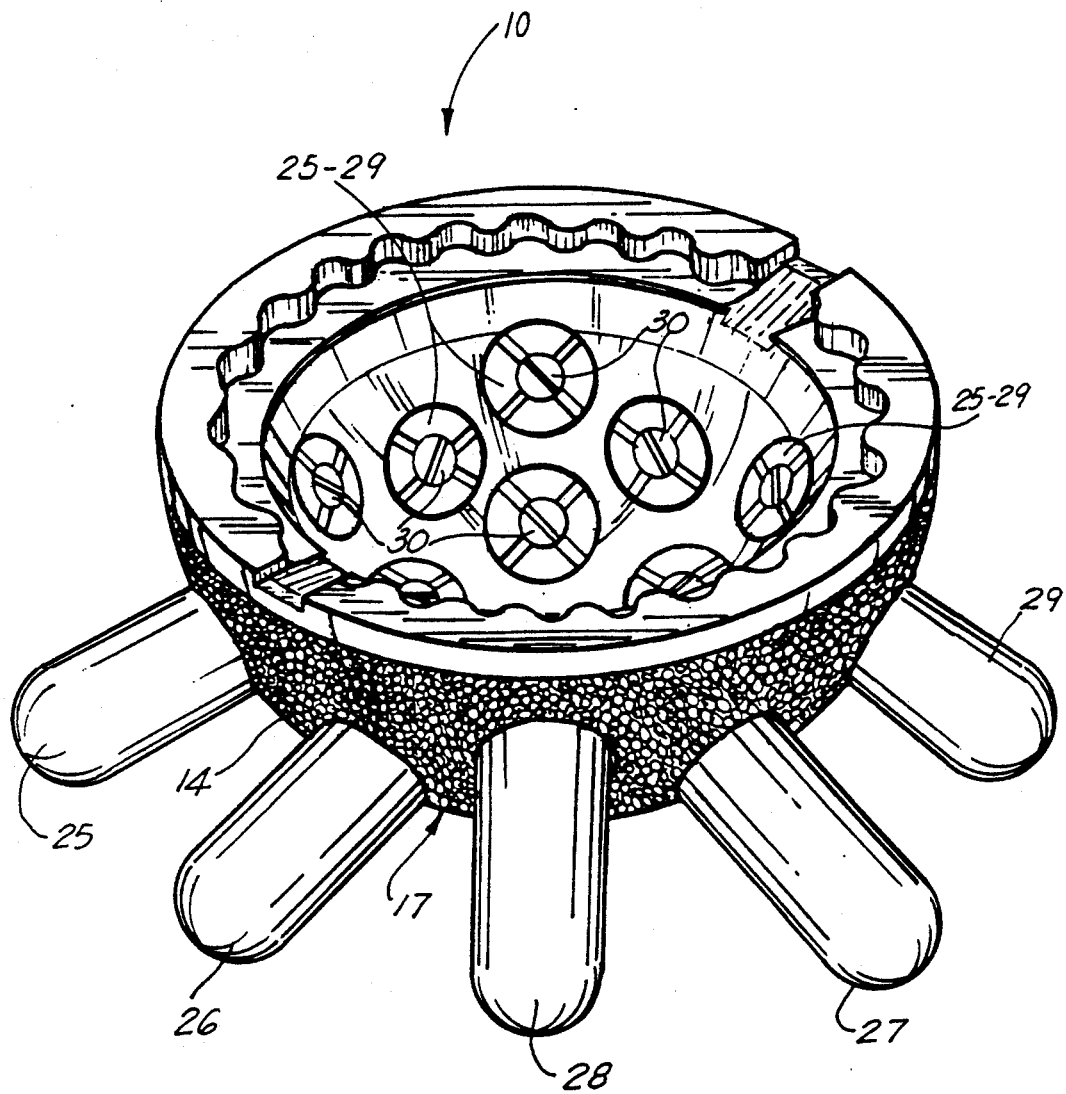
FIG. 2 is a perspective view of the preferred embodiment of the apparatus of the present invention.

In FIG. 1 there can be seen a sectional view of the preferred embodiment of the apparatus of the present invention designated generally by the numeral 10. In FIG. 1, there can be seen a hip prosthesis member 11 mounted in a femur 12 of a patient. The hip prosthesis 11 includes an upper ball portion 13 that registers with the acetabular prosthetic apparatus 10 of the present invention. The acetabular prosthesis 10 includes a cup body 14, preferably of a metallic material with a plastic liner 15 portion. The metallic cup body 14 includes an inner concave surface 16 and an outer convex surface 17.

Figure 3:
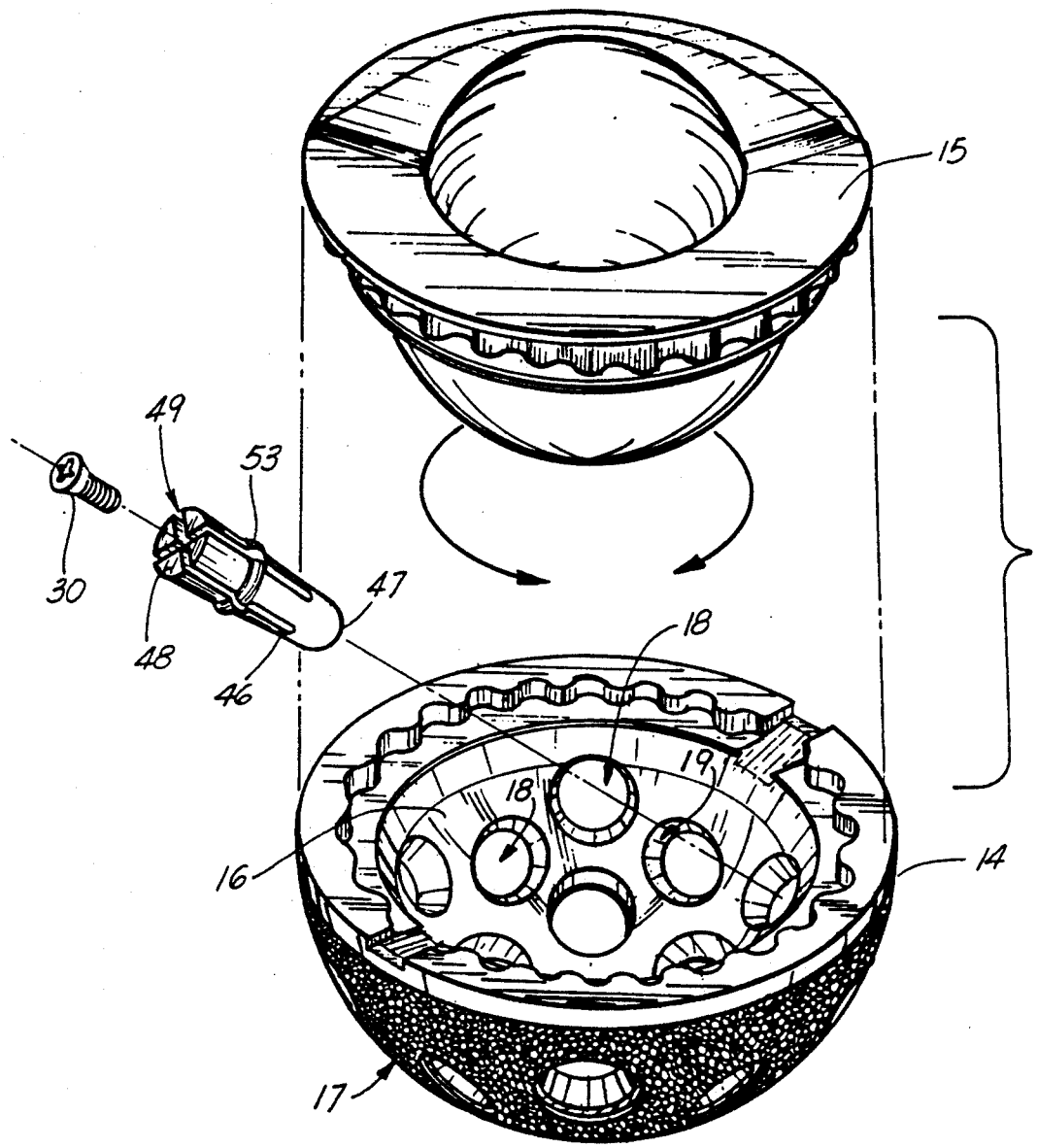
FIG. 3 is an exploded perspective view of the preferred embodiment of the apparatus of the present invention.

A plurality of openings 18 in form of preferably elongated bores extend between the inner concave surface 16 and the outer convex surface 17. These openings are in the form of bores having a bore wall 19 as seen in FIG. 3. The openings 18 can function as drill guides for the surgeon. Therefore, once the metallic cup body 14 portion of the acetabular cup prosthesis 10 is placed in position as shown in FIG. 1, the surgeon can simply drill through any one of the plurality of bores forming an opening in the underlying bone tissue designated generally be the numeral 20.

When the surgeon places the cup body 14 in the position shown in FIG. 1, the plurality of bores 18 can act as a drill guide for the surgeon, as the bore 19 walls of each opening 18 define a guide for a correspondingly sized drill so that the surgeon can penetrate and form surgical openings in the bone tissue 20. Each of the surgically formed openings 18 is then occupied by a peg (but not necessarily each hole item 18), such as one of the pegs 25-29, as seen in FIGS. 1-3 and 4A. In the preferred embodiment, each of the pegs 25-29 extends into the bone tissue at a different angular position with respect to the other pegs to provide a rigid anchor for the cup 14. Pegs 25-29 can be polymer, metal, or resorbable polymer.

Once the pegs 25-29 are placed into operative position, a strong connection is formed between the outer surface of each peg 25-28 and the walls 19 of each opening or bore 18. In FIGS. 5A-5C, 6A-6C, 7A-7C, and 8-11, various embodiments of the pegs, their respective attachments to the cup body 14 are illustrated.

Figure 8:
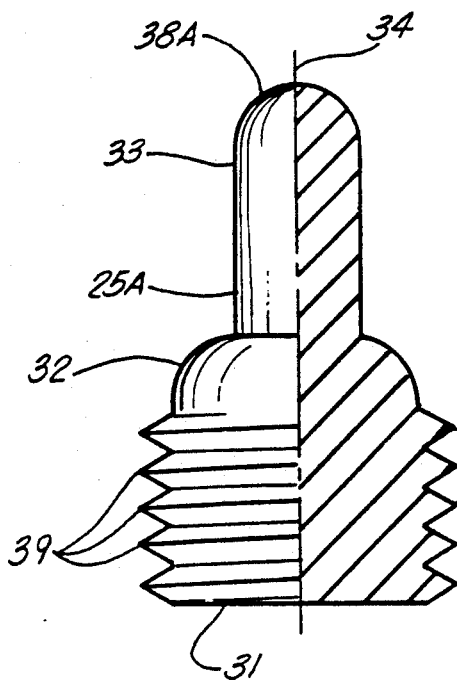
FIGS. 8, 9, 10, and 11 are peg members used with the preferred embodiment of the apparatus of the present invention including respectively thread lock, barb lock, taper lock, and knurl lock embodiments thereof.

In FIG. 8, peg 25A includes a proximate end portion 31 and a distal end portion 38A and a central longitudinal axis 34. A smaller diameter section 33 connects with a larger diameter section 32 that is covered with an external spiralling thread 39. The thread 39 bites into and interfaces with the cup body 14 at the wall 19 of each opening 18. The opening or bore 18 wall 19 can also be internally threaded to engage the thread 39.

Figure 9:
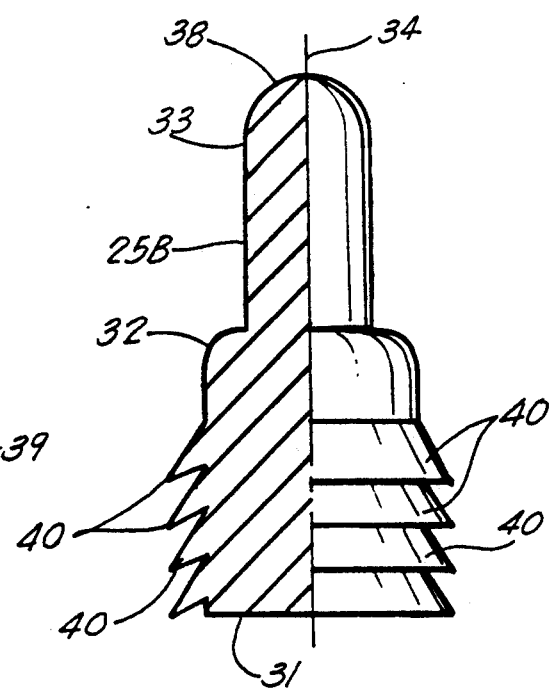

In FIG. 9, peg 25B is provided with a proximate end 31, a distal end 38, a smaller diameter section 33, and a larger diameter section 32 that carries a plurality of annular barb rings 40. When the peg 25B is forced into the opening 18, the barbs 40 form a tight fit with the cup body 14 at the wall 19 of each opening 18.

Figure 10:
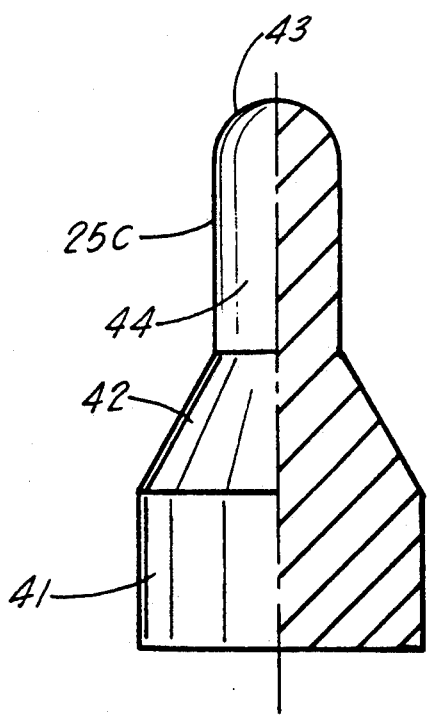
Figure 11:
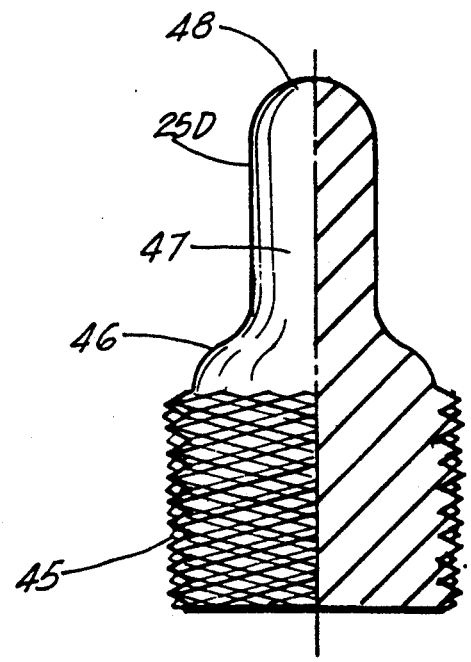
Figure 15:
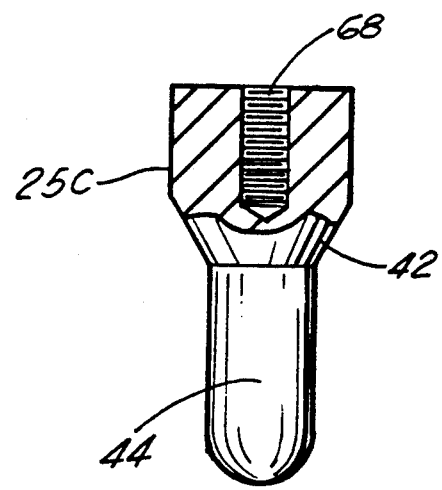
FIG. 15 is a partial sectional view illustrating the peg of FIG. 10.

In the embodiment of FIGS. 10, 11 and 15, peg 25C, 25D provide provides a proximate, larger diameter 41 end portion, a smaller generally cylindrical distal end portion 44, and a transitional frustro-conical section 42, and a curved end 43. Similarly, peg 25D has a proximate, larger diameter 45 portion, a curved annular transitional section 46, a smaller and generally cylindrical section 47, and a curved end portion 48. The large diameter section 41 and the frustro-conical portion 42 can also be seen in FIG. 15 in a partial sectional view. The larger diameter and frustro-conical sections 41, 42 surround an internally threaded bore 68 which accepts set screw 30. The screw 30 is sized to expand the enlarged 41 and frustro-conical 42 sections slightly when the peg 25C is placed in position within one of the bores 18 which would be similar in shape to the outside surface of frustro-conical portion 42 and enlarged portion 41. When the set screw 30 is fully threaded into the threaded opening 68, so that the external thread 67 of the set screw 30 engages the internal thread 68 of the bore, a taper lock connection or interference fit is formed between the peg 25C and the wall 19 of opening 18. Internal threads 68 in FIG. 15 can also be used as an extraction or holding means for placing and removing the peg 25c. Peg 25c would be used then without a screw 30.

Figure 12A:
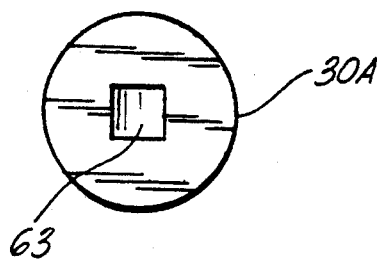
FIGS. 12A-12D are alternate constructions of a locking pin member used with the taper locking embodiment of the spike.
Figure 12B:
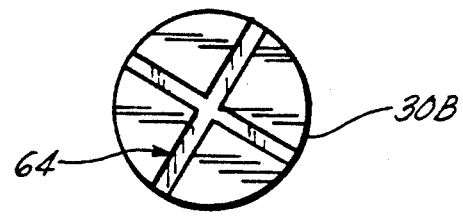
Figure 12C:
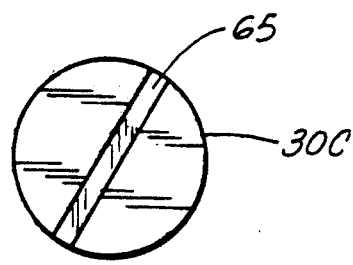
Figure 12D:
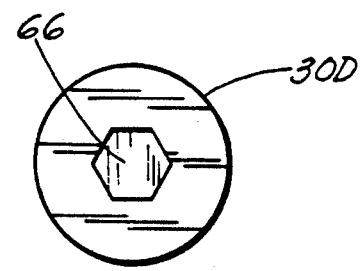
Figure 13:
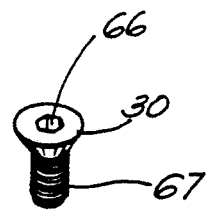
FIG. 13 is a perspective fragmentary view of the preferred embodiment of the apparatus of the present invention illustrating the peg locking screw portion thereof.
Figure 14:
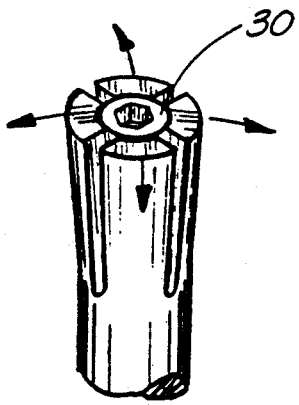
FIG. 14 is a perspective fragmentary view of one embodiment of the apparatus of the present invention illustrating an interface of the peg locking screw with one of the pegs of FIGS. 5A-5C.

The set screw 30 can have different tooled sockets, as shown in FIGS. 12A-12D. In FIG. 12A, a set screw 30A includes a square tooled socket 63. In FIG. 12B, the set screw 30B has a X-shaped slot 64 for receiving a Phillips-type screwdriver, for example. In FIG. 12C, the set screw 30C has a single transverse slot 65 and in the embodiment of FIG. 12B, the set screw 30B has an hexagonal tool socket 66. Other tooled sockets could be employed.

Figure 4A:
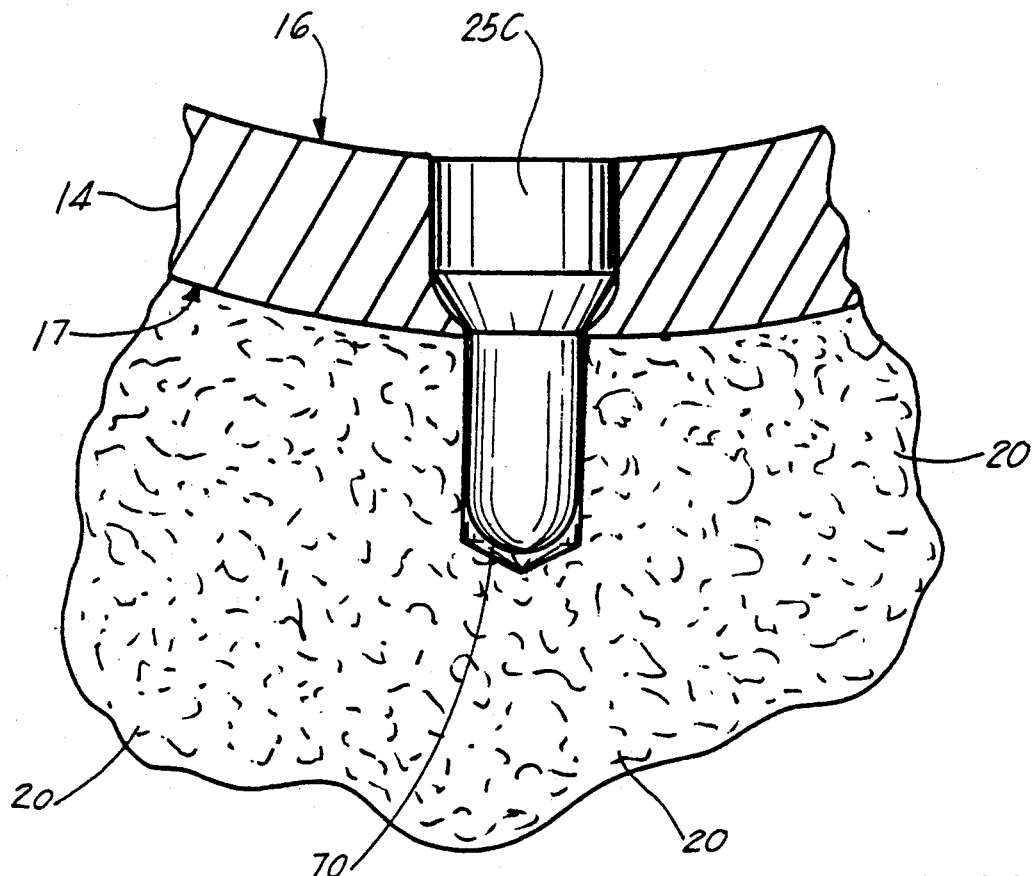
FIG. 4-4A are fragmentary views of the preferred embodiment of the apparatus of the present invention.
Figure 4:
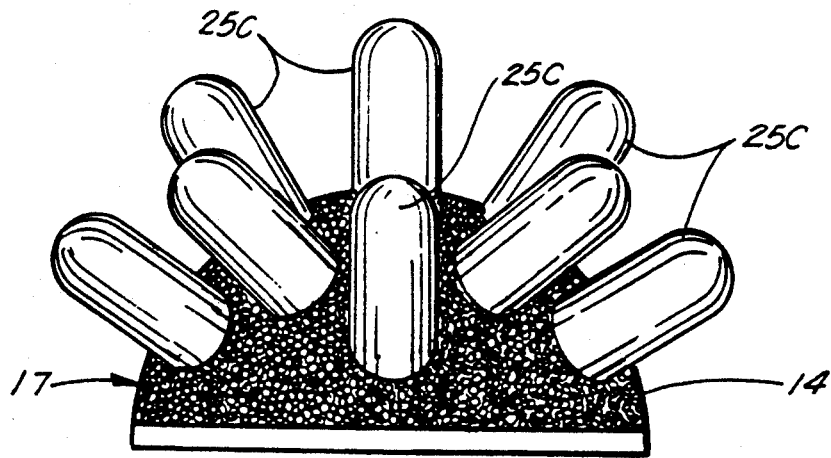

In FIGS. 4-4A, the pegs 25C can be shown extending from the convex 17 surface of cup body 14 and into a surgically formed opening 70 which is formed by the drill that penetrates the opening 18. In such a situation, the surgeon simply uses the opening 18 as a drill guide for a similarly shaped drill when forming surgical opening 70.

In FIGS. 5A-5C, an alternate construction of peg is illustrated designated generally by the numeral 50A. Peg 50A includes a rounded or hemispherical end portion 51 and a proximate end portion 52 that includes a pair of longitudinally extending slots 49, forming four peg sections 55.

In the embodiments of FIGS. 6A-6C, the peg 50B provides a hemispherical tip 51 and a single longitudinally extending transverse slot 52 forming two peg sections 55. Enlarged annular shoulder 53 and smaller diameter recess 54 are also provided in each of the embodiment of FIGS. 5A-5C and 6A-6C.

In the embodiment of FIGS. 7A-7C, a spike-shaped peg 56 is provided having a pointed tip portion 57, and a plurality of beveled surfaces 58 that connect with a cylindrical peg body portion that includes an enlarged annular section 60 and a smaller diameter constricted section 59. The proximate 61 end portion of the peg includes a longitudinally extending Y-shaped slot 62, as seen in FIGS. 7B and 7C.

Because many varying and different embodiments may be made within the scope of the inventive concept herein taught, and because many modifications may be made in the embodiments herein detailed in accordance with the descriptive requirement of the law, it is to be understood that the details herein ar to be interpreted as illustrative and not in a limiting sense.

What is claimed as the invention is:

1. An acetabular cup prosthesis, comprising:
    a) an acetabular cup body having an inner concave surface and an outer convex surface;
    b) a plurality of openings, each with a central axis that extends between the inner and outer surfaces, and the axes defining lines that converge near a center of curvature of the inner concave surface, the openings forming elongated bores surrounded by a bore wall portion of the acetabular cup body;
    c) at least some of the openings being configured to define one or more drill guides so that a surgeon can drill into the underlying tissue and form surgical openings therein via one or more of the openings;
    d) at least one peg member, each being insertable into and registering respectively with one of the openings, each peg member having a first proximal end portion having means thereon for forming a rigid connection with the acetabular cup body at one of the openings and with the bore wall so that the cup body and pegs move together rather than relative to one another during use;
    e) the peg member having an elongated second distal end portion having a substantial length to extend into the underlying tissue after the cup body has been implanted in a patient; and
    f) the distal end portion being substantially smooth so that peg movement will not disrupt adjacent bone tissue.

2. The apparatus of claim 1, wherein the inner concave and outer convex surfaces are of corresponding curvature.

3. The apparatus of claim 1, wherein each of the openings has a generally cylindrically shaped bore portion.

4. The apparatus of claim 1, wherein the elongated bores include a generally cylindrical portion and a generally frusto-conical portion.

5. The apparatus of claim 1, wherein the plurality of peg members are each generally cylindrical in configuration.

6. The apparatus of claim 1, wherein each of the plurality of peg members include a peg member having a section of larger diameter and a section of smaller diameter.

7. The apparatus of claim 1, wherein each of the plurality of peg members include a first larger diameter proximate end portion and a second smaller diameter distal end portion.

8. The apparatus of claim 1, wherein each peg member has a central longitudinally extending bore and the connection forming means includes means for expanding the peg diameter at the central longitudinal bore.

9. The apparatus of claim 1, wherein the acetabular cup body is of a metallic material at the bores.

10. The apparatus of claim 1, wherein the connection forming means communicates with the first proximate end portion of the peg member.

11. The apparatus of claim 1, each peg member has a longitudinally extending slot that allows at least a portion of the peg member to flex so that its diameter can be changed during insertion of the peg into a bore of the acetabular cup body.

12. The apparatus of claim wherein each peg member forms an interference fit with the openings.

13. The apparatus of claim 1 wherein each peg member has a longitudinally extending slot that allows the peg to deflect laterally in places along its length.

14. The apparatus of claim 1 wherein at least some of the pegs have rounded distal end portions.

15. The apparatus of claim 1 wherein at least some of the pegs have pointed, beveled end portions.

16. The apparatus of claim 1 further comprising means for expanding the diameter of the peg after insertion into the opening.

17. The apparatus of claim 16 wherein the peg has a longitudinally extended opening.

18. The apparatus of claim 1 wherein the peg is of a variable diameter including an enlarged proximate end portion and a smaller diameter distal type portion and the enlarged diameter portion has means for forming a tight fit with the opening.

* * * * *